United States Patent [19]
Thienpont

[11] Patent Number: 5,981,596
[45] Date of Patent: Nov. 9, 1999

[54] METHOD FOR THE CONTROL OF RESISTANT POPULATIONS OF LEPIDOPTERA

[75] Inventor: Emmanuel Thienpont, Rosoy en Multien, France

[73] Assignee: American Cyanamid Company, Madison, N.J.

[21] Appl. No.: 09/002,717

[22] Filed: Jan. 5, 1998

[30] Foreign Application Priority Data

Jan. 6, 1997 [FR] France ................... 97400060

[51] Int. Cl.$^6$ .................................................. A01N 47/28
[52] U.S. Cl. ............................................................ 514/594
[58] Field of Search ............................................. 514/594

[56] References Cited

U.S. PATENT DOCUMENTS

| 4,666,942 | 5/1987 | Anderson | 514/594 |
| 4,698,365 | 10/1987 | Anderson | 514/594 |

OTHER PUBLICATIONS

Chemical Abstracts, vol., 116, No. 3, Jan. 20, 1992, abstract No. 17136, C. Peter et al, "Field tests with the new insect growth regulators for the control of diamondback moth Plutella xylostella L", XP002062799.

STN–accession No. 97:50695, S. Wu et al, "Resistance of the tobacco army moth (*Prodenia litura*) to insecticides and its control", XP002062800 (1995).

STN–accession No. 91:64634, S. Boscheri et al, "La difesa dei meleti on Alto Adige dal cemiostoma (Leucoptera scitella Zell.) mediante regolatori di crescita degli insetti", XP002062801 (1989).

STN–accession No. 93:65004, S. Rai et al, Chemical control of diamondback moth, XP002062802 (1992).

STN–accession No. 93:79386, G. H. Ernst et al, Acylureas, susceptibility of cotton pests in Central America, XP00206803 (1992).

STN–accession No. 97:147073, E. Thienpont et al, "Interet du flufenoxuron pour lutter contre les populations resistantes de carpocapse des pommes", XP002062804 (1997).

STN–accession No. 97–86323, C. Martinet, "Carpocapse des pommes et de poires. Un Mieux, Mais la riguer reste de mise", XP002062805 (1997).

Biological Abstracts, vol. 98, abstract No. 133791, D. Bylemans, "An integrated control of the tortricid complex (Tortricidae) in Belgium pome fruit orchards". (1997).

STN–accession No. 93–82320, R. Delorme, "La Resistance aux Insecticides et Acaricides chez les Arthropodes Phytophages en France", XP002062806 (1993).

*Primary Examiner*—Allen J. Robinson
*Attorney, Agent, or Firm*—John W. Hogan, Jr

[57] ABSTRACT

There is provided a method for the control of resistant populations of Lepidoptera: Olethreutidae such as *Cydia pomonella* (L.), *Laspeyresia pomonella* (L.) *Grapholitha molesta* (Busck), and the like and the protection of fruit crops therefrom which comprises contacting said Lepidoptera with a toxic amount of flufenoxuron.

15 Claims, No Drawings

METHOD FOR THE CONTROL OF RESISTANT POPULATIONS OF LEPIDOPTERA

BACKGROUND OF THE INVENTION

Fruit-eating Lepidoptera are an important worldwide pest. Even a small percentage of infestation can be economically more significant than the monetary value of the fruit, due to the increased cost of sorting before packing and the increased infestation potential for the ensuing season. Overwintering larvae, upon emerging from diapause enter fruit after blossom causing the first generation. As many as three generations may occur during a growing season, facilitating Lepidoptera populations to develop resistance to environmental toxins such as insecticides.

Although numerous insecticides may control Lepidoptera effectively, most require frequent application. As a result, the efficacy of the insecticides may be severely compromised by the development of resistant populations such as acylurea-resistant, pyrethroid-resistant, and organophosphate-resistant Lepidoptera.

Therefore, it is an object of this invention to provide a unique and highly effective compound useful for the control of resistant populations of Lepidoptera.

It is another object of this invention to provide a method to enhance the protection of fruit crops from the infestation and attack of acylurea-resistant, pyrethroid-resistant, and organophosphate-resistant Lepidoptera.

It is an advantage of this invention that the method of control of resistant Lepidoptera populations is non-harmful to beneficial insect species and is fairly benign to the environment.

These and other features and objects of the invention will become apparent from the detailed description set forth below.

SUMMARY OF THE INVENTION

The present invention provides a method for the control of resistant Lepidoptera which comprises contacting said Lepidoptera, their habitat, breeding area, or food supply with a toxic amount of 1-[4-(2-chloro-α, α, α-trifluoro-p-tolyloxy)-2-fluorophenyl]-3-(2,6-difluorobenzoyl) urea (flufenoxuron).

Also provided is a method for the enhanced protection of fruit crops both growing and harvested from attack and infestation of resistant Lepidoptera which comprises applying to said crops or the soil or water in which they are growing or container in which they are stored an effective amount of flufenoxuron.

DETAILED DESCRIPTION OF THE INVENTION

Resistance is a widespread phenomenon and resistant populations of many economically important pests can now be found. Lepidoptera resistant to acylurea, pyrethroid and organophosphate insecticides pose a serious problem to fruit crop protection worldwide.

Resistance is herein defined as: a heritable reduction in the sensitivity of an insect population to the action of a pesticide, the reduction being expressed as a decrease in the frequency of individual insects affected by exposure to the pesticide (in comparison to the frequency observed in the same population upon initial or prior exposure).

Benzoylurea compounds such as those described in U.S. Pat. No. 4,666,942 are known to be useful for the control of insects and acarids. However, it has now been found that the specific compound, 1-[4-(2-chloro-α, α, α-trifluoro-p-tolyloxy)-2-fluorophenyl]-3-(2,6-difluorobenzoyl) urea (flufenoxuron), is highly efficacious against resistant populations of Lepidoptera. In the specification and claims the term resistant populations designates acylurea-resistant, pyrethroid-resistant, carbamate-resistant, benzhydrazide-resistant and/or organophosphate-resistant populations.

Surprisingly, resistant populations of Lepidoptera of the order Olethreutidae such as *Cydia pomonella* (L.), *Laspeyresia pomonella* (L.), *Grapholitha molesta* (Busck), and the like, preferably *Cydia pomonella*, may be controlled by contacting said resistant Lepidoptera, their habitat, breeding grounds or food supply with a toxic amount of flufenoxuron. It is especially surprising that flufenoxuron, an acyl urea compound, is effective against acylurea-resistant populations of Lepidoptera.

Advantageously, flufenoxuron may be employed to enhance the protection of fruit crops, preferably pome fruit and stone fruit such as apple, pear, quince, apricot, peach and plum, more preferably pome fruit such as apple and pear, from damage caused by attack and infestation of said resistant Lepidoptera. The resistant Lepidoptera control and crop protection methods of use of this invention are non-harmful to beneficial insect species and are especially suitable for application in responsible pest management programs.

The effective amount of the flufenoxuron compound to be used in the method of invention will vary according to the mode of application used, the identity of the resistant Lepidoptera to be controlled, the degree of infestation, the nature of the target host, the time of application, the weather conditions and the like. Naturally, quantities of greater than effective amounts of the flufenoxuron compound may be applied, but are not required for protection of the target crop from the resistant Lepidoptera.

In actual practice, generally about 10 ppm to 10,000 ppm, preferably about 100 ppm to 5,000 ppm, of the flufenxuron compound of the invention dispersed in water or other inexpensive liquid carrier is effective when applied to the resistant Lepidoptera or to their habitat, breeding area or food supply. The flufenoxuron compound of the invention is also effective for controlling resistant Lepidoptera, preferably *Cydia pomonella*, when applied to the foliage, twigs, blossoms, or fruit of crops, or to the soil or water in which they are growing, or to the container in which the harvested fruit is stored, at rates of about 5.0 g/hL to 50 g/hL, preferably about 5.0 g/hL to 15 g/hL.

Advantageously, while the flufenoxuron of the invention may be employed alone for the effective control of resistant Lepidoptera populations, it may also be used in combination with other biological or chemical pest control agents such as other insecticides, fungicides, herbicides and the like.

Protection of fruit crops from the infestation and attack of resistant Lepidoptera, particularly *Cydia pomonella*, may be enhanced by the application of an effective amount of the flufenoxuron compound. Said compound may be applied as a spray, dust, powder, granule, or the like. A suitable composition comprises an effective amount of the flufenoxuron compound and an agriculturally acceptable inert liquid or solid carrier.

In order to present a more clear understanding of the invention, the following specific examples are set forth below. These examples are merely illustrative and are not to be understood as limiting the scope and underlying principles of the invention in any way. Indeed, various modifications of the invention, in addition to those illustrated and described herein, will become apparent to persons skilled in the art from the following examples and the foregoing description. Such modifications are also intended to fall within the scope of the appended claims.

EXAMPLE 1
Evaluation of the Effect of Flufenoxuron on Susceptible and Resistant Strains of Cydia pomonella In this evaluation, two C. pomonella strains, one susceptible and the other resistant, are bred on an artificial biological medium. The susceptible strain (S) is obtained from a laboratory-maintained source and the resistant strain (R) is obtained from a field in which the resistance level has been observed and subsequently maintained in the laboratory by deltamethrin selection pressure. Tests are carried out on young larvae which are placed on the treated media. Treatments are performed using flufenoxuron formulated as a dispersible concentrate (DC) at 100 g/L (CASCADEO® 100 DC). Observations are made 7 days after treatment. Data obtained are analyzed using the standard probit method to determine the lethal concentration(LC) required for 90% mortality ($LC_{90}$) for each strain [(R) and (S)] of C. pomonella and the concentration required to obtain 50% mortality ($LC_{50}$) of each strain. The results are shown in Table I.

TABLE I

Flufenoxuron Toxicity Against Susceptible And Resistant Strains Of C. pomonella

| C. pomonella STRAIN | $LC_{90}$ (PPM) | $LC_{50}$ (PPM) |
| --- | --- | --- |
| S | 11.72 | 3.29 |
| R | 12.95 | 3.85 |

As shown in Table I, no sensitivity difference to flufenoxuron is observed between the resistant and susceptible strains of C. pomonella.

The resistance ratio $LC_{50}$ (R)/$LC_{50}$ (S) is 1.17 for flufenoxuron. In comparison, the resistance ratio, estalished in similar tests for deltamethrin is about 50, and for diflubenzuron the resistance ratio is about 10,000.

Comparative Example 2
Field Evaluations of the Effect of Test Compounds on Resistant Lepidoptera In these evaluations, field sites with a high level of resistance to diflubenzuron, deltamethrin, or phosalone were chosen. All tests were performed in open fields having resistant C. pomonella populations. Treatments were applied using the following commercially available formulations:

Invention

| flufenoxuron - | CASCADE ™ 100 DC |
| --- | --- |
| | (100 g/L dispersible concentrate) |

Comparative Compounds

| azinphos-methyl - | GUSATHION ™ XL 25% WP |
| --- | --- |
| | (259 g/kg wettable powder) |
| diflubenzuron - | DIMILIN ™ 25% WP |
| | (250 g/kg wettable powder) |
| teflubenzuron - | DART ™ 150 SC |
| | (150 g/l suspension concentrate) |
| deltamethrin - | DECIS ™ 25 EC |
| | 25 g/l emulsifiable concentrate) |

Each field trial is reported in a separate table. Comparative compounds were tested at dosages commensurate with the recommended commercial use rates. Therefore, for susceptible populations, expected % efficacy values would be 80%–100%. The results are reported as % efficacy which designates the % of reduction of the frequency of attacked fruits.

To establish this % efficacy in each plot, untreated and treated, the total number of fruits (T) and number of attacked fruits (A) is counted. The % of attacked fruits is calculated as shown below.

$$A = \frac{A}{T} \times 100$$

The % Efficacy is calculated using Abbott's formula as shown below.

$$\% \text{ Efficacy} = \frac{\% A \text{ (untreated)} - \% A \text{ (treated)}}{\% A \text{ (untreated)}} \times 100$$

TABLE II

Field Evaluation of Test Compounds For the Protection Of Apples Against Damage Caused By Acylurea-Resistant Populations Of C. pomonella

| Active Ingredient | Dose g/hL | % Efficacy | % A (untreated) |
| --- | --- | --- | --- |
| flufenoxuron | 10.0 | 92 | — |
| azinphos-methyl | 43.75 | 89 | — |
| diflubenzuron | 10.0 | 23 | — |
| teflubenzuron | 5.0 | 63 | — |
| untreated | 0.0 | — | 49.9 |

TABLE III

Field Evaluation of Test Compounds For The Protection Of Apples Against Damage Caused By Acylurea-Resistant Populations Of C. pomonella

| Active Ingredient | Dose g/hL | % Efficacy | % A (untreated) |
| --- | --- | --- | --- |
| flufenoxuron | 10.0 | 95 | — |
| azinphos-methyl | 43.75 | 87 | — |
| diflubenzuron | 10.0 | 24 | — |
| untreated | 0.0 | — | 12.6 |

In the above field trials, the sites contained C. pomonella populations with a high resistance to diflubenzuron. As shown in the above Tables II and III, flufenoxuron demonstrated a high level of efficacy against acylurea-resistant strains of C. pomonella.

TABLE IV

Field Evaluation Of Test Compounds For The Protection Of Apples Against Damage Caused By Pyrethroid-Resistant Populations Of C. pomonella

| Active Ingredient | Dose g/hL | % Efficacy | % A (untreated) |
| --- | --- | --- | --- |
| flufenoxuron | 10.0 | 73 | — |
| azinphos-methyl | 43.75 | 69 | — |
| deltamethrin | 0.75 | 22 | — |
| untreated | 0.0 | — | 61.9 |

In this trial site, resistance to deltamethrin is very high. As can be seen in Table IV above, flufenoxuron demonstrated good control of the pyrethroid-resistant population.

TABLE V

Field Evaluation Of Test Compounds For The Protection of Apples Against Damage Caused By Organophosphate-Resistant Populations Of *C. pomonella*

| Active Ingredient | Dose g/hL | % Efficacy | % A (untreated) |
|---|---|---|---|
| flufenoxuron | 10.0 | 86 | — |
| phosalone | 60.0 | 10 | — |
| untreated | 0.0 | — | 99.1 |

In this trial site which is very highly infested, resistance to phosalone is high. As can be seen in Table V above, flufenoxuron demonstrated a high level of efficacy against the organophosphate-resistant population.

I claim:

1. A method for the control of resistant Lepidoptera, said Lepidoptera being of the order Olethreutidae, which comprises contacting said Lepidoptera, their habitat, breeding area, or food supply with a toxic amount of flufenoxuron.

2. The method according to claim 1 wherein the Lepidoptera are acylurea-resistant, pyrethroid-resistant and/or organophosphate-resistant.

3. The method according to claim 2 wherein the Lepidoptera are acylurea-resistant.

4. The method according to claim 1 wherein the Lepidoptera: Olethreutidae are selected from the group consisting of *Cydia pomonella, Laspeyresia pomonella*, and *Grapholitha molesta*.

5. The method according to claim 4 wherein the Lepidoptera are *Cydia pomonella*.

6. A method for the enhanced protection of fruit crops both growing and harvested from attack and infestation of resistant Lepidoptera, said Lepidoptera being of the order Olethreutidae, which comprises applying to said crops or the soil or water in which they are growing or locus in which they are stored an effective amount of flufenoxuron.

7. The method according to claim 6 wherein the Lepidoptera is acylurea-resistant.

8. The method according to claim 6 wherein the fruit crop is pome fruit or stone fruit.

9. The method according to claim 8 wherein the pome fruit or stone fruit are selected from the group consisting of apple, pear, quince, apricot, peach, and plum.

10. The method according to claim 9 wherein the pome fruit are apple or pear.

11. The method according to claim 10 wherein the Lepidoptera are *Cydia pomonella*.

12. The method according to claim 6 wherein the flufenoxuron is applied at a rate of about 5.0 g/hL to 50 g/hL.

13. The method according to claim 12 wherein the flufenoxuron is applied at a rate of about 5.0 g/hL to 15.0 g/hL.

14. The method according to claim 13 wherein the Lepidoptera is *Cydia pomonella*.

15. The method according to claim 14 wherein the Lepidoptera is acylurea-resistant.

* * * * *